United States Patent [19]

Brown

[11] 4,423,062

[45] Dec. 27, 1983

[54] CYANOVINYL PYRETHROIDS AND PESTICIDAL USE THEREOF

[75] Inventor: Dale G. Brown, Hopewell, N.J.

[73] Assignee: American Cyanamid Company, Stamford, Conn.

[21] Appl. No.: 341,973

[22] Filed: Jan. 22, 1982

Related U.S. Application Data

[60] Division of Ser. No. 124,153, Feb. 25, 1980, Pat. No. 4,325,969, which is a Continuation of Ser. No. 937,360, Aug. 28, 1978, abandoned.

[51] Int. Cl.$^3$ .................. A01N 43/02; A01N 37/34
[52] U.S. Cl. .................. 424/275; 424/282; 424/304; 542/429; 260/465 D
[58] Field of Search .................. 424/304, 282, 275; 542/429; 260/465 D

[56] References Cited

U.S. PATENT DOCUMENTS

| | | | |
|---|---|---|---|
| 3,973,036 | 8/1976 | Hirano et al. | 260/465 D |
| 3,997,586 | 12/1976 | Mortel et al. | 542/429 |
| 4,062,968 | 12/1977 | Fujimoto et al. | 260/465 D |
| 4,091,111 | 5/1978 | Ohno et al. | 424/275 |
| 4,157,447 | 6/1979 | Engel | 424/304 |
| 4,200,644 | 4/1980 | Engel | 424/275 |
| 4,262,117 | 4/1981 | Brown | 424/275 |

FOREIGN PATENT DOCUMENTS

3420  8/1979  European Pat. Off. ............ 424/304

*Primary Examiner*—Douglas W. Robinson
*Attorney, Agent, or Firm*—H. G. Jackson

[57] ABSTRACT

The invention relates to novel substituted cyclopropanecarboxylic acid esters, and to methods of preparation thereof. The invention also relates to methods of use of the compounds for the control of insect pests of agriculturally important crops, and for the control of ectoparasites, especially acarina, of domesticated warm-blooded animals.

4 Claims, No Drawings

CYANOVINYL PYRETHROIDS AND PESTICIDAL USE THEREOF

This is a division of application Ser. No. 124,153 filed Feb. 25, 1980 now U.S. Pat. No. 4,325,969 which in turn is a continuation of Ser. No. 937,360 filed Aug. 28, 1978, abandoned.

The invention relates to novel substituted cyclopropanecarboxylic acid esters, hereinafter also referred-to as "cyanovinyl pyrethroids", together with methods of use for the control of insect pests of agriculturally important crops and of ectoparasites, especially acarina, of domesticated warm-blooded animals.

Control of the above insect pests of crops comprises applying an effective amount of a compound of the invention to the foliage and stems of the crops and/or to the soil in which these crops propagate and grow. Control of the ectoparasites, especially acarina, can be best achieved by contacting the ectoparasites with an effective amount of a compound of the invention or by applying an effective amount of the compound topically to the host animal and/or treating their environment with same. Alternatively, these compounds may be used for systemic control of the ectoparasites, especially acarina, comprising administering to the host animal orally or parenterally an effective amount of the substituted cyclopropanecarboxylic acid esters of the invention. These novel compounds may be represented and defined by formula (I) as follows:

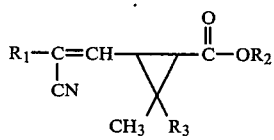

wherein $R_1$ is

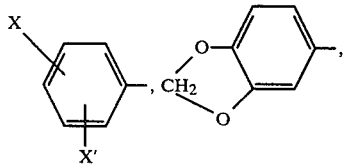

$R_2$ is a moiety selected from

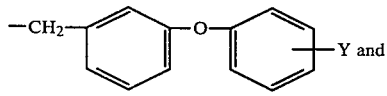

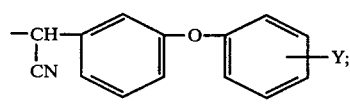

$R_3$ is hydrogen or methyl; X and X' are each selected from hydrogen, halogen, $C_1$-$C_3$ alkyl, $C_1$-$C_3$ alkoxy and haloalkyl $C_1$-$C_2$; Y is selected from hydrogen, halogen, methyl or methoxy. It is recognized of course, that the compounds represented by formula (I) above may exist in a number of geometric and optical isomeric forms and mixtures thereof, and that varying degrees of insecticidal and acaricidal activity would be expected to be associated with each isomer. Those isomers in which the carboxylic acid (ester) and the β-cyanostyryl functions are in the opposite sides of the cyclopropane ring are designated as trans; those in which they are on the same side are designated as cis. In each case, these may be separated into (+) and (−) optical isomers by appropriate methods, such as, for instance, the use of chiral bases in the separation of the carboxylic acid precursors (of formula IV) of the above formula (I) compounds. A further locale for geometrical isomerism is the β-cyanostyryl function itself. In this case the designation Z is given to those compounds in which the cyano and cyclopropyl substituents are on the same side of the carbon-carbon double bond, whereas the E isomer is that in which the aryl or heterocyclic and the cyclopropyl substituents are so situated.

When the formula IV acids are esterified with α-cyano-m-phenoxybenzyl alcohol, the resulting formula (I) esters have an additional chiral center. It is recognized that certain molecular species combining special combinations of these geometrical and optical characteristics will possess superior insecticidal and acaricidal activity. The invention includes all such combinations. Thus, the hereinabove defined compounds of formula (I) may be the cis and trans cyclopropane isomers, the E and Z side-chain olefin isomers, the optical isomers thereof and the isomeric mixtures thereof.

A preferred group of compounds represented by formula (I) above are those wherein $R_1$ is selected from

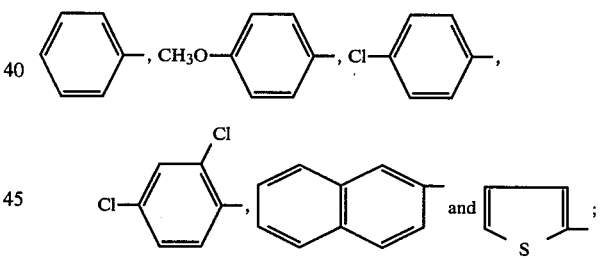

$R_2$ is selected from

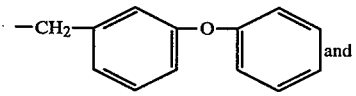

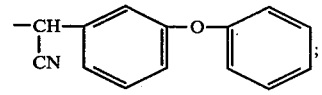

$R_3$ is methyl; the cis and trans cyclopropane isomers, the E and Z side-chain olefin isomers, the optical isomers thereof and the isomeric mixtures thereof.

Among the economic losses caused annually by acarina, those attributable to the sub-order Ixodidae are of considerable importance. Ixodid ticks are responsible for the maintenance and propagation of a great many human and animal diseases throughout the world. They are vectors for the diseases: tick paralysis and tick toxicosis. A single tick species can cause paralysis of several different mammals, and several tick species can cause paralysis in a particular host. Tick-borne diseases, such as Sweating Sickness, Babesiosis, Anaplasmosis, Theileriosis and Heartwater, have been and are responsible for the death and/or debilitation of a vast number of animals throughout the world each year. In point of fact, of all external parasites, ticks are responsible for the greatest economic losses in livestock production in the world today. Such losses are, of course, attributed not only to death, but also damaged hides, loss in growth rate, reduction in milk production and reduced grade of meat animals.

The hereinabove described and defined compounds represented by formula (I) are eminently suitable for the control of Ixodidae. Control is effected by means of ixodicidal and of chemosterilant activity which the formula (I) compounds exert upon the larvae, nymphs, and adult male and female ticks. This method of control is useful against Argasidae or Ixodidae ticks, including, for example, those of the following types: Boophilus, Amblyomma, Anocentor, Dermacentor, Ixodes, Haemaphysalis, Hyalomma, Rhipicentor, Margaropus, Rhipicephalus, Argas, Otobius, and Ornithodorus.

Conveniently, the compounds represented by formula (I) may be prepared by the following reaction sequence:

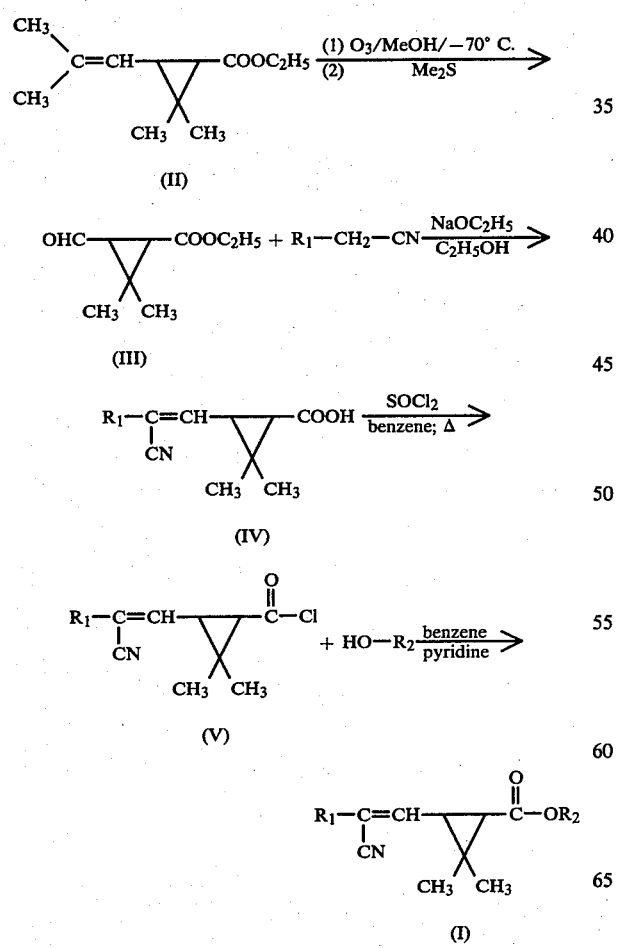

wherein in the above reaction sequence $R_1$ and $R_2$ are as hereinbefore defined and $R_3$ was chosen to represent $CH_3-$.

Thus, ethyl chrysanthemate (II), wherein $R_3$ is methyl, is oxidized with ozone in a methanolic solution at $-50°$ to $-70°$ C. to yield the corresponding 3-formyl-2,2-dimethylcyclopropanecarboxylic acid ethyl ester (III). Next, the thus obtained formyl compound is condensed in the presence of a base, such as sodium ethoxide in a lower alcohol with a compound of formula: $R_1-CH_2-CN$ having an active methylene group to yield a cyclopropanecarboxylic acid of formula (IV). This acid is converted to the corresponding acid chloride (V) with thionyl chloride in an inert aromatic solvent such as benzene, toluene or xylene. The acid chloride (V) is then reacted with an alcohol of formula $R_2-OH$ in the presence of an acid acceptor, such as pyridine, in an inert aromatic solvent such as benzene, toluene or xylene to afford the desired cyclopropanecarboxylic esters of formula (I).

Alternatively, formula (I) compounds may be prepared from the corresponding cyclopropanecarboxylic acids via ester forming reactions promoted by phase transfer catalysts. The above referred-to reactions may be schematically illustrated as follows:

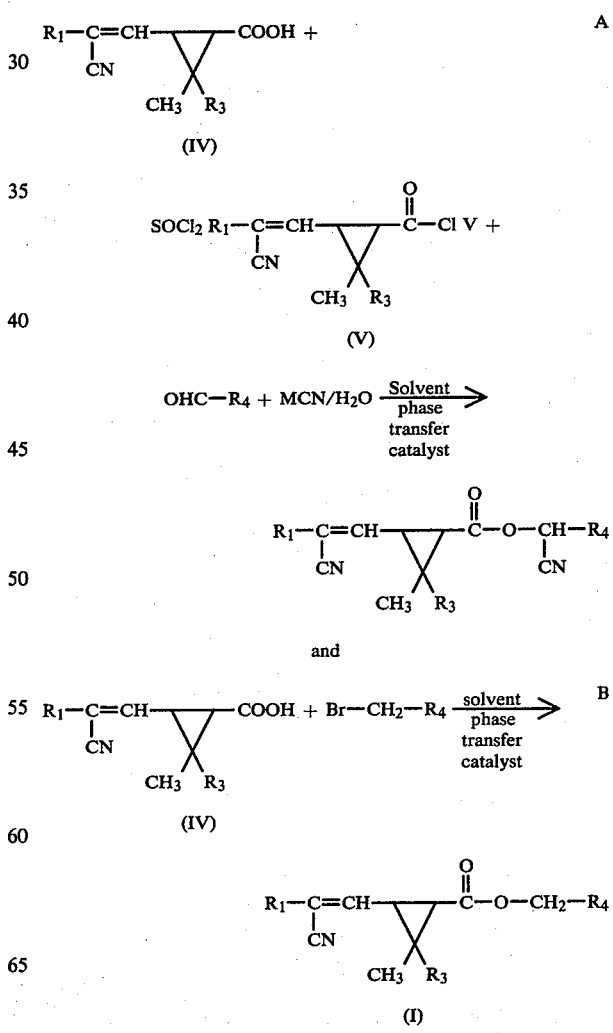

wherein in the above reaction schemes A and B, $R_1$ is selected from

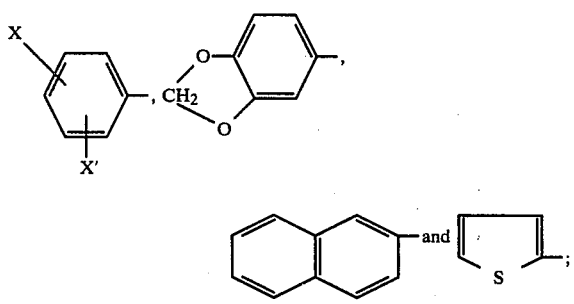

$R_3$ is selected from hydrogen or methyl; $R_4$ is

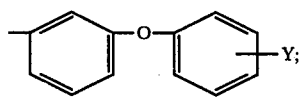

M is sodium or potassium; X and X' are each selected from hydrogen, halogen, $C_1$–$C_3$ alkyl, $C_1$–$C_3$ alkoxy and haloalkyl $C_1$–$C_2$; Y is selected from hydrogen, halogen, methyl or methoxy; the cis and trans cyclopropane isomers, the E and Z side-chain olefin isomers the optical isomers thereof and the isomeric mixtures thereof.

In the above reactions, the phase transfer catalysts are selected from benzyltriethylammonium chloride, benzyl-tri-n-propylammonium chloride, α-methylbenzyltriethylammonium iodide, tetrabutylammonium chloride and iodide, methyl tricaprylammonium chloride, hexadecyl trimethylammonium bromide, benzyl triphenylphosphonium chloride, hexadecyl tributyl phosphonium bromide, crown ethers, such as 18-crown-6, dicyclohexyl-18-crown-6 and dibenzo-18-crown-6. These phase transfer catalysts are utilized in amounts of 0.1% to 10% molar quantities and preferably 5% to 10% molar quantities. Solvents for these reactions are selected from methylene chloride, chloroform, 1,2-dichloroethane, hexane, heptane cyclohexane, benzene, toluene, xylene and ethyl acetate. The above described reactions are further illustrated in the Examples appended hereto.

Control of Ixodids is achieved by contacting the larvae, nymphs and the adult males and females with the cyclopropanecarboxylic esters of formula (I). Application can be made directly or indirectly. It is generally effected by topically applying the active ingredients, namely the compounds of formula (I) onto the host to be protected or to the habitat of the Ixodid.

Application is generally facilitated by employing a composition containing an effective amount of a compound of formula (I) in combination with an inert agricultural adjuvant. One or more of the conventional solid or liquid carriers, diluents and formulation aids may be employed as the adjuvant. Furthermore, in addition to employing a single compound of formula (I) as the active ingredient, several of the formula (I) compounds, or one or more of the compounds in combination with conventional pesticides may be employed.

The compounds of the invention as represented by formula (I) may be conveniently formulated as dusts, dust concentrates, wettable powders, emulsifiable concentrates, and the like. Application thereof is made in conventional manners, such as, by spraying, dusting, dipping in baths, and the like.

Solid formulations such as dusts, dust concentrates, can be prepared by grinding and blending together an inert solid diluent such as attapulgite, kaolin, walnut shell flour, diatomaceous earth, ground corncob grits, or ground coconut shell, and the active ingredient where such ingredient is in solid form. Where the active ingredient is a liquid, it may be sprayed on the carrier and thoroughly mixed therewith, or it may be dissolved in a solvent such as acetone, lower alkanol, toluene, xylene and the like, and sprayed as a dilute solution on the solid carrier. Dusts usually contain from about 1% to 15% by weight of active ingredient, whereas concentrates may contain from about 16% to about 85% by weight of the active material.

Wettable powders are prepared in the same fashion as dust concentrates excepting that about 5% to 10% by weight of a surfactant is also added. The wettable powder is then generally dispersed in water, or other suitable diluent for application as a dilute spray onto the Ixodid, host or locus where control is desired or as a bath for dipping animal hosts.

The formula (I) cyclopropanecarboxylic acid esters may also be prepared as emulsifiable concentrates by dissolving or dispersing about 10% to 75% by weight of the active compound in a suitable solvent carrier such as a petroleum distillate having a minimum aromatic content of 85%, and admixing therewith about 10% by weight of an emulsifier such as polyoxyethylene condensates and blends of same with alkyl aryl sulfonates. These concentrates are also generally dispersed in water or other suitable solvent for application by spraying or dipping the animal host.

Application of the formula (I) compounds at rates in the range of from about 1 ppm to 250 ppm for the control of ectoparasites, and especially Ixodidae, is generally preferred.

For the control of insect pests of agriculturally important crops application at rates in the range of from about 10 ppm to 1000 ppm is generally preferred.

The following non-limiting Examples further serve to illustrate the invention.

EXAMPLE 1

Preparation of 3-formyl-2,2-dimethyl-cyclopropanecarboxylic acid, ethyl ester

A solution of ethyl chrysanthemate (156.0 g) in absolute methanol (1400 ml) is stirred, cooled to −65° C., and ozone bubbled in at a rate of 1.7 l/min. under 0.56 kg/cm² pressure (the ozone is generated with a Welsbach T-23 ozonator; voltage setting 120 VAC). During the reaction, the temperature range of the reaction mixture fluctuates between −65° C. and −50° C.

The reaction is followed with gas chromatography [6'×¼" glass column, packed with 3% OV-1 on WHP; temperature 130° C.; sample size 0.2 λ; flow 45 ml/min He; FID detector] to measure the disappearance of ethyl chrysanthemate. The ozonolysis is stopped after about 6 to 7 hours when about 5% ethyl chrysanthemate is still present. Methyl sulfide (125 ml) is added over 20 minutes, and the reaction mixture allowed to warm up to room temperature overnight with stirring. Next, the methanol is removed in vacuo at 50°–55° C. The residual oil is diluted with ether, and the ether solution washed with water. The ether layer is dried over magnesium sulfate, filtered, and is then evaporated to yield 131.3 g of title product.

An nmr is run on the product to determine if any acetal which may have formed during the reaction (multiplet at 3.4 δ) is present. If acetal is found in the product, 10% hydrochloric acid (85ml) is added with stirring followed by the addition of sufficient amount of tetrahydrofuran to obtain a homogeneous solution. The solution is heated at 40°–50° C. for one hour. Water and ether are added, and the aqueous layer extracted with ether. The ether layers are combined, dried over magnesium sulfate and evaporated in vacuo to afford the title product.

EXAMPLE 2

Preparation of (Z)-cis and trans-3-(β-cyanostyryl)-2,2-dimethyl-cyclopropanecarboxylic acid Phenylacetonitrile is added to a stirred solution of sodium ethoxide in absolute ethanol (prepared from 1.1 g sodium and 100 ml of ethanol). Next, a solution of 3-formyl-2,2-dimethyl-cyclopropanecarboxylic acid ethyl ester (8.5 g) in absolute ethanol (15 ml) is added over 5 minutes. The reaction mixture is stirred for 12 hours at room temperature and then heated on a steam bath for 0.5 hour. The alcohol is removed in vacuo, and the residue washed with water (250 ml) and ether (150 ml). The aqueous layer is acidified with concentrated hydrochloric acid. The resulting cream colored slurry is filtered and the isolated product dried. The product is dissolved in ether and precipitated with hexane to afford 6.1 g of white crystals, m.p. 186°–188° C.

By the above procedure, a number of cyclopropanecarboxylic acids are prepared. These are listed in Table I below, together with their melting points.

TABLE I
Substituted Cyclopropanecarboxylic Acids

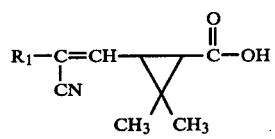

| $R_1$ | m.p. °C. |
|---|---|
| 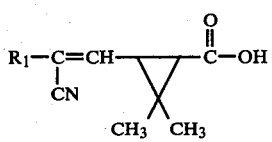 | 190–208 |
| 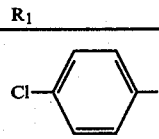 | 188–198 |
| 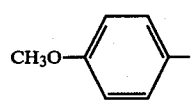 | 120–142 |
| 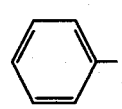 | 130–145 |
| 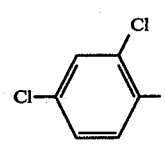 | |

TABLE I-continued
Substituted Cyclopropanecarboxylic Acids

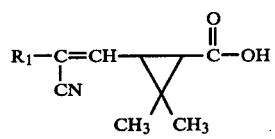

| $R_1$ | m.p. °C. |
|---|---|
| 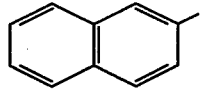 | 217–218 |
| 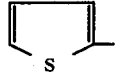 | 140–143 |
| 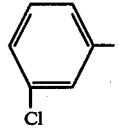 | 125–155 |
| 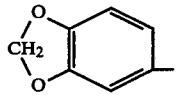 | 160–180 |
| 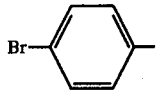 | 179–195 |
| 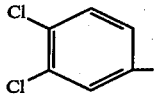 | 195–202 |
| 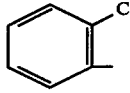 | * |
| 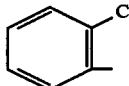 | 103–112 |
| 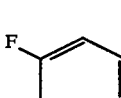 | 150–164 |
| 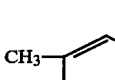 | 164–176 |
| 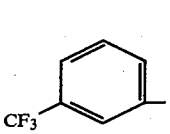 | 117–123 |

* = Gum - NMR TMS - CDCl₃ doublet - 6.30δ doublet 7.05δ

EXAMPLE 3

Preparation of (Z)-trans-3-(β-cyanostyryl)-2,2-dimethylcyclopropanecarboxylic acid m-phenoxybenzyl ester A mixture of (Z)-cis and trans-3-(β-cyanostyryl)-2,2-dimethyl-cyclopropanecarboxylic acid (3.5 g), benzene, (50 ml), and thionyl chloride (3.4 g) is refluxed for 1 hour. The benzene and excess thionyl chloride are then removed in vacuo. The residue is dissolved in benzene and added to a solution of m-phenoxybenzyl alcohol (2.9 g) in a mixture of benzene (50 ml) and pyridine (1.1 g). The reaction mixture is stirred at room temperature for 3 hours, and then filtered. The filtrate is evaporated in vacuo. The residue is chromatographed on a silica gel column, and eluted with ethyl acetate and hexane to afford the title product. Analysis calculated for $C_{28}H_{25}O_3N$: C 79.41; H 5.95; N 3.31; Found: C 78.58; H 6.41; N 2.84.

By the above procedure, a number of cyclopropanecarboxylic acid esters are prepared. These are listed in Table II below, together with the corresponding analytical data.

TABLE II
Cyclopropanecarboxylic acid esters

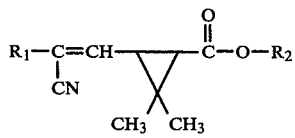

| $R_1$ | $R_2$ | Analysis Calculated | Found |
|---|---|---|---|
|  | CMPB | C 77.66<br>H 5.39<br>N 6.24 | C 76.65<br>H 5.71<br>N 5.88 |
|  | MPB | C 73.43<br>H 5.28<br>N 3.06 | C 73.35<br>H 5.44<br>N 2.89 |
|  | CMPB | C 72.12<br>H 4.80<br>N 5.80 | C 71.44<br>H 5.25<br>N 5.03 |
|  | MPB | C 76.80<br>H 6.00<br>N 3.09 | C 76.02<br>H 5.89<br>N 2.61 |
|  | CMPB | C 75.29<br>H 5.48<br>N 5.86 | C 74.93<br>H 5.35<br>N 5.68 |
|  | MPB | C 68.30<br>H 4.71<br>N 2.85 | C 68.25<br>H 4.72<br>N 2.55 |
|  | CMPB | C 67.32<br>H 4.29<br>N 4.90 | C 66.64<br>H 4.46<br>N 4.90 |
|  | CMPB | C 79.50<br>H 5.26<br>N 5.62 | C 79.20<br>H 5.69<br>N 5.54 |
|  | CMPB | — | — |

TABLE II-continued

Cyclopropanecarboxylic acid esters

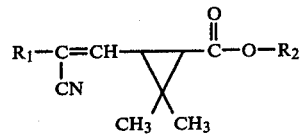

| R₁ | R₂ | Analysis Calculated | Found |
|---|---|---|---|
| 3-Cl-C₆H₄- | MPB | C 73.58<br>H 5.25<br>N 3.04 | C 72.34<br>H 5.65<br>N 2.86 |
| 3-Cl-C₆H₄- | CMPB | C 72.12<br>H 4.80<br>N 5.80 | C 71.47<br>H 5.10<br>N 5.42 |
| 3,4-methylenedioxyphenyl- | MPB | C 74.50<br>H 5.39<br>N 3.00 | C 73.25<br>H 5.48<br>N 2.85 |
| 3,4-methylenedioxyphenyl- | CMPB | C 73.16<br>H 4.91<br>N 5.69 | C 71.59<br>H 5.22<br>N 5.33 |
| 4-Br-C₆H₄- | MPB | C 66.93<br>H 4.81<br>N 2.79 | C 66.33<br>H 4.97<br>N 2.64 |
| 4-Br-C₆H₄- | CMPB | C 66.04<br>N 4.40<br>N 5.31 | C 65.58<br>H 4.74<br>N 4.95 |
| 3,4-di-Cl-C₆H₃- | MPB | C 68.30<br>H 4.71<br>N 2.85 | C 68.60<br>H 4.84<br>N 2.58 |
| 3,4-di-Cl-C₆H₃- | CMPB | C 67.32<br>H 4.29<br>N 5.42 | C 66.55<br>H 4.64<br>N 5.13 |
| 2-Cl-C₆H₄- | MPB | C 73.44<br>H 5.28<br>N 3.06 | C 73.12<br>H 5.25<br>N 2.71 |

TABLE II-continued

Cyclopropanecarboxylic acid esters

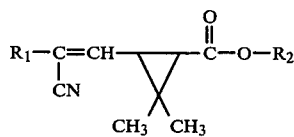

| $R_1$ | $R_2$ | Analysis Calculated | Found |
|---|---|---|---|
| 2-Cl-C₆H₄ | CMPB | C 72.12<br>H 4.80<br>N 5.80 | C 70.85<br>H 5.03<br>N 5.22 |
| 2,3-Cl₂-C₆H₃ | MPB | C 68.30<br>H 4.71<br>N 2.85 | C 67.83<br>H 4.98<br>N 2.59 |
| 2,3-Cl₂-C₆H₃ | CMPB | C 67.32<br>H 4.29<br>N 5.41 | C 65.13<br>H 4.11<br>N 5.14 |
| 4-F-C₆H₄ (trans) | MPB | C 76.17<br>H 5.48<br>N 2.86 | C 75.29<br>H 5.63<br>N 2.80 |
| 4-F-C₆H₄ (cis) | MPB | C 76.17<br>H 5.48<br>N 2.86 | C 76.52<br>H 5.61<br>N 2.69 |
| 4-F-C₆H₄ | CMPB | C 74.67<br>H 4.97<br>N 6.00 | C 74.64<br>H 5.15<br>N 5.90 |
| 4-CH₃-C₆H₄ (trans) | MPB | C 79.61<br>H 6.22<br>N 3.20 | C 79.39<br>H 6.44<br>N 3.01 |
| 4-CH₃-C₆H₄ (cis) | MPB | C 79.61<br>H 6.22<br>N 3.20 | C 79.33<br>H 6.22<br>N 2.85 |
| 4-CH₃-C₆H₄ | CMPB | C 77.90<br>H 5.67<br>N 6.06 | C 74.54<br>H 5.36<br>N 5.63 |

TABLE II-continued
Cyclopropanecarboxylic acid esters

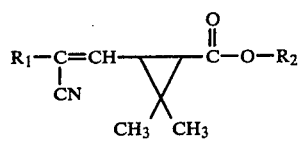

| R₁ | R₂ | Analysis Calculated | Found |
|---|---|---|---|
| phenyl | -CH(CN)-C₆H₄-O-C₆H₄-F | C 74.67<br>H 4.97<br>N 6.00 | C 74.32<br>H 5.11<br>N 5.55 |
| phenyl | -CH(CN)-C₆H₄-O-C₆H₄-OCH₃ | C 75.30<br>H 5.48<br>N 5.85 | C 74.02<br>H 5.49<br>N 5.84 |
| phenyl | -CH(CN)-C₆H₄-O-C₆H₄-Cl | C 72.11<br>H 4.80<br>N 5.80 | C 72.43<br>H 4.97<br>N 5.52 |

MPB = —CH₂—C₆H₄—O—C₆H₅

CMPB = —CH(CN)—C₆H₄—O—C₆H₅

EXAMPLE 4
Preparation of 2-Formyl-3-methylcyclopropanecarboxylic acid ethyl ester Crotonaldehyde (14.0 g; 0.2 mole) is added dropwise to a gently refluxing solution of tetrahydrothiophene ylid (34.0 g; 0.2 mole) in dry acetone (200 ml). Heating at reflux is continued for about 15 minutes after the addition is completed, then the reaction mixture is concentrated on a rotary evaporator at 50° C. Distillation of this concentrate at reduced pressure affords 15.32 g (49.1%) of title product, a pale yellow oil, b.p. 0.1 mm, 44°–45° C. The structure is confirmed by IR and NMR.

EXAMPLE 5
Preparation of (Z)-cis and trans-2-(β-cyanostyryl)-3-methylcyclopropanecarboxylic acid A solution of sodium ethoxide is prepared by adding sodium spheres (1.15 g, 0.05 mole) to absolute ethanol (100 ml) with stirring until a solution is obtained. Phenylacetonitrile (5.86 g, 0.05 mole) and 2-formyl-3-methylcyclopropanecarboxylic acid methyl ester (7.81 g, 0.05 mole) are added to the above solution at room temperature. The resultant clear solution is stirred for 18 hours at room temperature, then heated at reflux for about 0.5 hours. The reaction mixture is then cooled, evaporated in vacuo, and the residue dissolved in water. The aqueous solution is extracted (3X) with ether and is then acidified with concentrated hydrochloric acid. A brown solid precipitates and is isolated by filtration and dried to afford 8.78 g (77.3%) of a tacky brown solid. NMR data supports the presence of both isomers (the olefin proton of the two isomers appearing as doublets at 6.17 ppm and 6.96 ppm).

EXAMPLE 6
Preparation of (Z)-cis and trans-2-(β-cyanostyryl)-3-methylcyclopropanecarboxylic acid, α-cyano-m-phenoxybenzyl ester By the procedure of Example 3, (Z)-cis and trans-2-(β-cyanostyryl)-3-methylcyclopropanecarboxylic acid (5.0 g, 0.022 mole) is reacted with thionyl chloride (d=1.63; 1.75 ml), 0.24 mole), and when formation of the acid chloride is complete, it (the acid chloride) is further reacted with a mixture of α-cyano-m-phenoxybenzyl alcohol (4.5 g, 0.02 mole) and pyridine (1.74 g, 0.022 mole) to yield a crude, gummy product. The crude is purified by dry column chromatography tograpphy silica gel; 1:1 methylene chloride (hexane) to give 4.8 g (57.1%) of a yellow gum. Analysis calculated for C₂₈H₂₂N₂O₃: C 77.40; H 5.10; N 6.45; Found: C 76.30; H 5.23; N 6.24.

EXAMPLE 7
Preparation of (Z)-cis and trans-3-(β-cyano-p-methylstyryl)-2,2-dimethyl-cyclopropanecarboxylic acid, m-phenoxybenzyl ester m-Phenoxybenzylbromide (3.68 g; 0.014 mole) is added to a solution of 3-(β-cyano-p-methylstyryl)-2,2-dimethylcyclopropanecarboxylic acid (3.19 g; 0.0125 mole) and triethylamine (1.27 g; 0.0125 mole) in dry dimethylformamide and the reaction mixture stirred for 18 hours at room temperature. The reaction mixture, containing some precipitated salts, is poured into water and extracted with ether (2×75 ml). The combined ether extracts are washed several times with water, then with sodium bicarbonate solution and saturated sodium chloride solution. Evaporation of the ether solution yields 3.42 g (62.5%) of a yellow oil. Purification of this yellow oil by dry column chromatography (silica gel; eluent: 1:1 methylene chloride:hexane) affords 0.96 g of the trans isomer and 0.6 g of the cis isomer.

Analysis calculated for $C_{29}H_{27}NO_3$: C 79.61; H 6.22; N 3.20; (trans) Found: C 79.39; H 6.44; N 3.01; (cis) Found: C 79.33; H 6.53; N 2.85.

EXAMPLE 8

Preparation of (Z)-cis and trans-3-(β-cyanostyryl)-2,2-dimethyl-cyclopropanecarboxylic acid, α-cyano-m-(p-chlorophenoxy)benzyl ester by a phase transfer catalyst esterification process Thionyl chloride (1.61 ml, 2.6 g; 0.022 mole), 3-(β-cyanostyryl)-2,2-dimethyl-cyclopropanecarboxylic acid (4.82 g; 0.02 mole) and toluene are mixed and heated at 100° C. for 1 hour. The reaction mixture is cooled to 25° C. and a solution of m-(p-chlorophenoxy)-benzaldehyde (4.65 g; 0.02 mole) and 18-crown-6 (0.49 g; 0.002 mole) in toluene (10 ml) is added. To this reaction mixture a solution of potassium cyanide (2.6 g; 0.04 mole) in water (6 ml) is added slowly while maintaining the temperature between 20°-25° C. The reaction mixture is then stirred for 18 hours at room temperature. The resultant black reaction mixture is poured in water and extracted with ether (3x). The combined ether extracts are washed with water, 10% hydrochloric acid, 10% sodium bicarbonate, water and saturated sodium chloride solution. The ether layer is dried over sodium sulfate and evaporated in vacuo to leave a brown gum. This gum is purified by dry column chromatography (silica gel; eluent: 1:1 methylene chloride:hexane) to afford the title product, a yellow glass (1.0 g, 8.6%).

Analysis calculated for $C_{29}H_{23}ClN_2O_3$: C 72.12; H 4.80; N 5.80; Found: C 72.43; H 4.97; N 5.53.

EXAMPLE 9

Preparation of 20% w/w emulsifiable concentrates containing cyanovinyl pyrethroids of the invention Toxicants (1). (Z)-trans-3-(p-chloro-β-cyanostyryl)-2,2-dimethylcyclopropanecarboxylic acid, α-cyano-m-phenoxybenzyl ester.

(2). (Z)-trans-3-(β-cyanostyryl)-2,2-dimethylcyclopropanecarboxylic acid, α-cyano-m-phenoxybenzyl ester.

(3). (Z)-trans-3-(2,4-dichloro-β-cyanostyryl)-2,2-dimethylcyclopropanecarboxylic acid, α-cyano-m-phenoxybenzyl ester.

| Component | Concentrates wt. in g. |
|---|---|
| Toxicant | 15.0 |
| Atlox ® 3403F/3404F; 50:50 mixture[a] | 10.125 |
| xylene | 6.75 |
| "HAN"[b] | 35.625 |
| Total: | 67.500 |

[a]Atlox ® 3403F, a polyoxyethylene alkyl aryl ether - alkyl aryl sulfonate blend; nonionic surfactant; specific gravity: 1.02 at 20° C.; wt in kg/l = 1.018 (8.5 lb/gal); approximate viscosity at 25° C. = 130 cps; flash point (C.O.C.; °F.) = 100;
Atlox ® 3403F, a polyoxyethylene ether polyoxyethylene glyceride - alkyl aryl sulfonate blend; anionic surfactant; specific gravity 1.05 at 25° C; wt in kg/l = 1.052 (8.7 lb/gal); approximate viscosity at 25° C. = 3700 cps; flash point (C.O.C.; °F.) = 160. Both are proprietary products of ICI United States Inc. Atlas Chemicals Division, Wilmington, Delaware.

[b]"HAN" = Heavy Aromatic Naphtha, boiling range 165° C. to 282° C.; Mixed aniline point °C. = 28.0; freeze point °C. = 36; aromatic content: 80%.

Method of preparation

The toxicant is preheated to about >85° C. to obtain a flowable melt, and then mixed with the surfactants, xylene and "HAN". The resultant mixture is heated and stirred to obtain a clear solution.

Standard emulsification test (50 λ/33 ml medium hard water) indicates, that although on addition the emulsifiable concentrate tends to float on top of the water layer, with agitation (or shaking) good emulsions are obtained, which remain quite stable with very little creaming on top.

The average micelle sizes of the aqueous emulsions prepared from the above concentrates are determined using a Coulter Counter with the following results:

| Emulsion containing toxicant No. | Micelle size in microns |
|---|---|
| 1 | 4.5 |
| 2 | 2.2 |
| 3 | 2.4 |

EXAMPLE 10

Evaluation of the efficacy of the compounds of the invention for the control of *Boophilus microplus* larvae Effective control of acarina larvae is demonstrated in the following tests with larvae of *Boophilus microplus*, a one-host tick which can remain on a single host through its three life stages, i.e. larva, nymph and adult. In these tests a 10% acetone/90% water mixture contains the test compound at the concentrations indicated in Table III below. Twenty larvae are enclosed in a pipet sealed at one end with a gauze material, and a solution, containing the test compound at the concentrations given, is then drawn through the pipet with a vacuum hose simulating a spray system. The ticks are then held for 48 hours at room temperature, and percent mortality rates are then determined. The results obtained with the various compounds are tabulated in Table III below.

TABLE III

Efficacy of cyanovinyl pyrethroids for the control of *Boophilus microplus* larvae.

$$R_1-\underset{\underset{CN}{|}}{C}=CH-\underset{\underset{CH_3\ CH_3}{\triangle}}{}\overset{O}{\underset{\|}{C}}-OR_2$$

| $R_1$ | $R_2$ | Concentration of Toxicant in spray solution (ppm) | Percent Mortality of *Boophilus microplus* larvae. |
|---|---|---|---|
| phenyl | CMPB | 0.001 | 100 |
| 4-Cl-phenyl | MPB | 0.001 | 100 |
| 4-Cl-phenyl | CMPB | 0.001 | 100 |
| 4-CH₃O-phenyl | MPB | 1.0 | 100 |
| 4-CH₃O-phenyl | CMPB | 1.0 | 100 |
| 2,4-diCl-phenyl | MPB | 0.001 | 100 |
| 2,4-diCl-phenyl | CMPB | 0.001 | 100 |
| 2-naphthyl | CMPB | 100.0 | 100 |
| 4-CH₃-phenyl (Z)-cis | MPB | 100 | 100 |

MPB = —CH₂—(3-phenoxyphenyl)

CMPB = —CH(CN)—(3-phenoxyphenyl)

TABLE III-continued

Efficacy of cyanovinyl pyrethroids for the control of *Boophilus microplus* larvae.

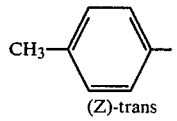

| $R_1$ | $R_2$ | Concentration of Toxicant in spray solution (ppm) | Percent Mortality of *Boophilus microplus* larvae. |
|---|---|---|---|
| 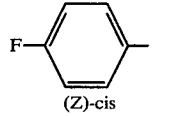 4-CH$_3$-C$_6$H$_4$- (Z)-trans | MPB | 100 | 100 |
| 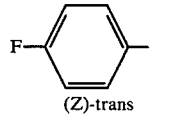 4-F-C$_6$H$_4$- (Z)-cis | MPB | 10 | 100 |
| 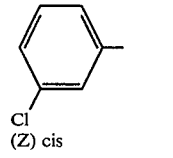 4-F-C$_6$H$_4$- (Z)-trans | MPB | 100 | 30 |
| 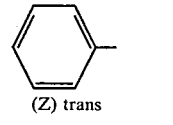 3-Cl-C$_6$H$_4$- (Z) cis | MPB | 100 | 100 |
| C$_6$H$_5$- (Z) trans | MPB | 100 | 0 |
| 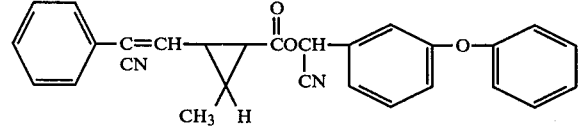 | | 1.0<br>0.1 | 100<br>50 |

EXAMPLE 11

Suppression of fecundity and chemosterilant effect in Ixodidae

The efficacy of the compounds of the invention for suppression of fecundity and chemosterilant effect in ticks is demonstrated in the following tests wherein engorged adult female *Boophilus microplus*, multiple resistant strain, ticks which have dropped from cattle are collected and used for testing.

The compound to be tested is dissolved in a 35% acetone/65% water mixture in amounts sufficient to provide the concentrations indicated in Table IV below. The ticks per treatment are used and they are immersed in the test solution for three to 5 minutes, then removed and held in incubators for two to three weeks at 28° C. Counts of ticks laying eggs are then made and recorded. Eggs which were laid are placed in containers and kept for one month to observe hatching and to determine chemosterilant effect. Results of these tests are given in Table IV below.

TABLE IV

Efficacy of cyanovinyl pyrethroids expressed as % reduction of viable egg masses.

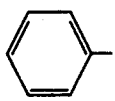

| $R_1$ | $R_2$ | Concentration in solution (ppm) | Percent reduction of viable egg masses |
|---|---|---|---|
| phenyl | CMPB | 31.2 | 95.9–99 |
|  |  | 16.0 | 85 |
|  |  | 8.0 | 65 |
|  |  | 8.0 | 84–94 |
|  |  | 4.0 | 62–70 |
| 4-Cl-phenyl | MPB | 15 | 99.4 |
|  |  | 8 | 72.9–78 |
|  |  | 4 | 24.5–32 |
| 4-Cl-phenyl | CMPB | 4 | 99.4 |
|  |  | 2 | 97 |
| 4-CH$_3$O-phenyl | MPB | 250 | 85.5–87.9 |
|  |  | 125 | 79.1–91.2 |
|  |  | 62 | 90.9–96.6 |
|  |  | 31 | 63.6 |
| 4-CH$_3$O-phenyl | CMPB | 31 | 91.8 |
|  |  | 15 | 73.5 |
| 2,4-di-Cl-phenyl | MPB | 32 | 85.6–91 |
|  |  | 16 | 87.5–95 |
|  |  | 8 | 40–64 |
| 2,4-di-Cl-phenyl | CMPB | 4 | 97 |
|  |  | 2 | 55 |
| 3-Cl-phenyl | CMPB | 31 | 98.8 |
| 2-naphthyl | CMPB | 15 | 92 |
| 2-thienyl | CMPB | 100 | 100 |

MPB = —CH$_2$—C$_6$H$_4$—O—C$_6$H$_5$ (3-phenoxybenzyl)

CMPB = —CH(CN)—C$_6$H$_4$—O—C$_6$H$_5$ (α-cyano-3-phenoxybenzyl)

EXAMPLE 12

Evaluation of the efficacy of cyanovinyl pyrethroids for the control of *Boophilus microplus* on cattle

Test Compounds

The 20% w/w emulsifiable concentrates of Example 6 are used in this experiment. Spray emulsions are prepared just prior to use from the above concentrates by diluting 11.25 ml and 22.5 ml of each with 75 liter of water to yield spray emulsions containing 30 and 60 ppm of active ingredient, respectively.

Test Animals

Holstein calves, 6 to 12 months old are experimentally infested with about 5000 larval ticks of a multiple resistant (resistant to organophosphate acaricides as well as to toxaphene and lindane) strain placed on each animal three times a week, starting 35 days pre-treatment. Three pre-treatment tick counters are made in days -6, -5 and -4. Calves are allocated to groups of five on the basis of these counts. One group serves as infected nontreated controls and one group each is used to evaluate the test compounds at 30 and 60 ppm level of toxicant, respectively. On treatment day, each animal is sprayed with a total of 15 liters of emulsion delivered at 21.09 kg/cm$^2$ pressure with a "Teejet 8002 Excelsior" nozzle providing a fan-shaped spray. Mortality counts (female ticks 4.5–8.0 mm) are taken over days 2 to 21 posttreatment for a total of 9 times. Residual effect is measured by six mortality counts taken over days 23 to 35 posttreatment. The results obtained, are summarized and tabulated in Table V below.

TABLE V

Evaluation of the efficacy of the compounds of the present invention for the control of multiple resistant ticks on cattle.

| R$_1$ | Toxicant Concentration (ppm) | Percent Mortality (post-treatment) Days 2 to 21 | Days 23 to 35 |
|---|---|---|---|
|  | 30 | 95.8 | 97.8 |
| | 60 | 99.2 | 99.4 |
| 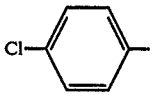 | 30 | 92.9 | 99.2 |
| | 60 | 96.8 | 99.2 |
| 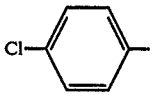 | 30 | 65 | 89.2 |
| | 60 | 85.9 | 95.5 |

EXAMPLE 13

Evaluation of the Ixodicidal activity of cyanovinyl Pyrethroids against *Amblyomma hebreum*

The ixodicidal activity of the compounds of the invention is demonstrated in the following tests wherein juvenile adult *Amblyomma hebreum* ticks are collected and used for testing.

The compound to be tested is dissolved in a 35% acetone/65% water mixture in amounts sufficient to provide the concentrations indicated in Table VI below. Ten ticks per treatment (ten males or ten females) are used and they are immersed in the test solution for three to 5 minutes, then removed and held in incubators at 28° C. Percent mortality is determined at 24 and 96 hours post-immersion. The data obtained is tabulated in Table VI below.

TABLE VI

Percent Mortality of *Amblyomma hebreum* at 24 hours post-immersion.

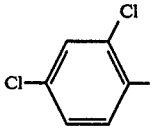

| R$_1$ | Concentration of Toxicant (ppm) | % Mortality at 24 hours | Remarks |
|---|---|---|---|
| 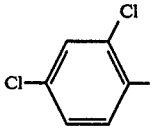 | 240 | 100 | 100% at 96 hours |
| | 120 | 100 | |
| | 60 | 90 | 75% at 96 hours |
| | 30 | 45 | |
| | 15 | 6 | |
| | 7.5 | 15 | |
| | 3.25 | 0 | |

TABLE VI-continued

Percent Mortality of *Amblyomma hebreum* at 24 hours post-immersion.

| R$_1$ | Concentration of Toxicant (ppm) | % Mortality at 24 hours | Remarks |
|---|---|---|---|
|  | 240 | 95 | |
| | 120 | 70 | |
| | 60 | 45 | |
| | 30 | 75 | |
| | 15 | 15 | |
| | 7.5 | 0 | |
| | 3.25 | 0 | |
|  | 240 | 100 | |
| | 120 | 100 | |
| | 60 | 65 | |
| | 30 | 60 | |
| | 15 | 50 | |
| | 7.5 | 0 | |
| | 3.25 | 0 | |

EXAMPLE 14

Evaluation of the efficacy of the compounds of the invention for the control of face flies (*Musca autumnalis*)

The cyanovinyl pyrethroids in these tests are dissolved in acetone to afford stock solutions at a concentration of 1000 ppm each.

One kg of fresh, untreated cow manure and the appropriate volume of the stock solution of the pyrethroid used in the test are mixed for two minutes with a Hobart heavy duty mixer to yield a blend containing the toxicant at the ppm concentration indicated in Table VII below. Control samples are prepared similarly using the corresponding volumes of acetone (no toxicant). Two 148 cm$^3$ (5-oz) plastic dixie cups are then mounded full of treated or untreated manure. A small reservoir is made in the top of the manure, and into this reservoir are placed twenty two-day old *Musca autumnalis* larvae. The larvae are then covered with the same manure. Each cup is placed in an individual sand tray for pupation, and maintained for 5 days. At the end of the period mortality counts are made. The results are given in Table VII below.

TABLE VII

Activity of Cyanovinyl pyrethroids for the control of *Musca autumnalis*

| $R_1$ | $R_2$ | Concentration (ppm) | Percent Mortality of *Musca autumnalis* |
|---|---|---|---|
|  | CMPB | 1<br>0.1 | 100<br>83 |
| 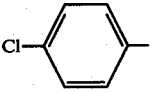 | MPB | 10 | 100 |
| 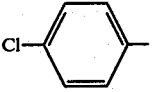 | MPB | 10 | 100 |
| 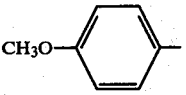 | CMPB | 1<br>0.1 | 83<br>100 |
| 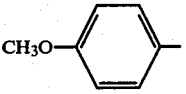 | MPB | 10 | 70.8 |
| 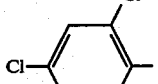 | CMPB | 10 | 100 |
| 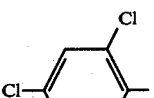 | MPB | 10 | 100 |
| 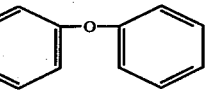 | CMPB | 10 | 84.7 |

MPB = 

CMPB = 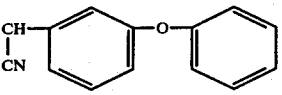

EXAMPLE 15

Evaluation of cyanovinyl pyrethroids for the control of Screwworm fly (*Cochliomyia hominivorax*) larvae

Screwworm Larvae

Newly hatched larvae are obtained after incubation of 100–120 mg egg masses placed on filterpaper, wetted with isotonic saline solutions in petri dishes, and kept at 27° C. and 80%–90% RH for 12–15 hours. The hatches larvae are reared on the following medium and maintained at 37° C.:

| Lean ground beef | 57.0 g |
|---|---|
| Bovine plasma | 21.4 ml |
| Water | 21.3 ml |
| Formalin | 0.3 ml |
| | Total: 100.0 |

After 48 hours, larvae are transferred to trays containing a slightly different medium and maintained in a water bath at 39°–40° C.:

| Lean ground beef | 40.0 g |
|---|---|
| Citrated bovine blood | 20.0 ml |
| Water | 39.7 ml |
| Formalin | 0.3 ml |
| | Total: 100.0 |

Two ml of an acetone-water solution, containing 10 times the final desired concentration of toxicant, is mixed with 18 g of nutritional medium in a 60-ml jar. The mixture is kept in a water bath at 39°–40° C. for about 30 minutes, i.e., until the medium reaches the same temperature. Then masses of 200–300 newly hatched screwworm larvae added to each jar containing the toxicant mixed with the nutritional medium. Larvae are picked up with a cardboard spatula from the petri dish where they had been incubated. Special care is taken to place larval masses over an "island" in the plasma medium. A new spatula is used for each concentration of toxicant. The jars are covered with a piece of muslin and kept in a water bath at 40° C. to the end of the experiment. Two replicates are used per concentration. Controls containing no toxicant but the highest concentration of acetone in the nutrient medium are kept for each experiment.

Final check, by visual inspection is made on the surface of the media after 48 hours, and the approximate percent mortality determined.

The results obtained are averaged and tabulated in Table VIII below.

TABLE VIII

Efficacy of cyanovinyl pyrethroids expressed as percent mortality of Screwworm Fly larvae.

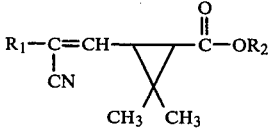

| $R_1$ | $R_2$ | Concentration of toxicant (ppm) | Percent Mortality of Screwworm Fly larvae (approximate) |
|---|---|---|---|
|  | CMPB | 25 | 100 |
|  |  | 5 | 21.1 |
|  | MPS | 25 | 34.1 |
|  | CMPB | 25 | 90 |
|  |  | 5 | 7 |
|  | CMPB | 25 | 7.3 |

EXAMPLE 16

Evaluation of the siphonaptericidal activity of cyanovinyl pyrethroids

The siphonaptericidal activity of the compounds of this invention is demonstrated by the following tests wherein the cyanovinyl pyrethroids listed in Table IX below are utilized as the active ingredients. In these tests, ten adult fleas of the species *Ctenocephalides felis* are sprayed for 30 seconds with an acetone/water solution containing 50 and 10 ppm of the test compound, respectively. After this treatment, the fleas are maintained for 48 hours at room temperature and 80+% relative humidity. At the end of this period the fleas are examined and mortality counts made. The results are tabulated in Table IX below.

TABLE IX

Activity of cyanovinyl pyrethroids against *Ctenocephalides felis*.

| $R_1$ | Concentration of toxicant (ppm) | Percent Mortality of Ctenocephalides felis |
|---|---|---|
|  | 50 | 100 |
|  | 10 | 45 |
| 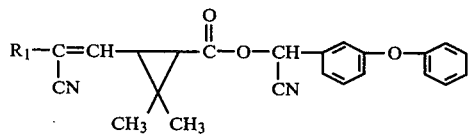 | 50 | 100 |
|  | 10 | 100 |

TABLE IX-continued

Activity of cyanovinyl pyrethroids against *Ctenocephalides felis*.

| $R_1$ | Concentration of toxicant (ppm) | Percent Mortality of Ctenocephalides felis |
|---|---|---|
|  | 50 | 90 |
|  | 10 | 100 |

EXAMPLE 17

Insecticide testing procedures

Malaria Mosquito (*Anopheles quadrimaculatus* say) egg and larvae test

One ml of a 300 ppm solution is pipetted into a 400 ml beaker containing 250 ml of deionized water and stirred with the pipette, giving a concentration of 1.2 ppm. A wax paper ring 0.6 cm wide to fit inside the beaker is floated on the surface of the test solution to keep the eggs from floating up the meniscus curve and drying out on the side of the glass. A spoon made of screen is used to scoop up and transfer about 100 eggs (0–24 hours old) into the test beaker. After two days at 26.7° C. observations of hatching are made. This includes kill of eggs or inhibition of hatch, kill of newly hatched larvae, or delayed hatch. Additional observations are made after another day for the same effects.

Tobacco Budworm [*Heliothis virescens* (Fabricius)]

A cotton plant with 2 true leaves expanded is dipped for 3 seconds with agitation in a 300 ppm solution. A 1.25 to 2 cm square of cheesecloth with about 50 to 100 budworm eggs 0–24 hours old is also dipped in the test solution and placed on one leaf to dry. The leaf with the treated budworm eggs is removed from the plant and placed in a 236.6 ml (8-oz) Dixie cup with a wet 5 cm piece of dental wick and covered with a lid. The other leaf is placed in a similar cup with a wick and a piece of cheesecloth infested with 50–100 newly hatched larvae is added before covering the cup with a lid. After 3 days at 26.7° C., observations of egg hatch are made as well as kill of newly hatched larvae, any inhibition of feeding, or interference of any sort with normal development.

Phosphate-Resistant Strain of Two-Spotted Spider Mite [*Tetranychus urticae* (Koch)]

Sieva lima bean plants, with primary leaves 7.6 to 10 cm long, are infested with about 100 adult mites per leaf 4 hours before use in this test, in order to allow egg-laying before treatment. The infested plants are dipped for 3 seconds with agitation into a 300 ppm solution, and the plants set in the hood to dry. After 2 days at 26.7° C., the adult mite mortality is estimated on one leaf under a 10X stereoscopic microscope. The other leaf is left on the plant an additional 5 days and then examined at 10X power to estimate the kill of eggs and of newly-hatched nymphs, giving a measure of ovicidal and residual action, respectively.

Southern Armyworm [*Spodoptera eridania* (Cramer)]

A Sieva lima bean plant with just the primary leaves expanded to 7.6 to 10 cm is dipped for 3 seconds with agitation in a 1000 ppm solution and set in a hood to dry. Following this, one leaf is placed in a 10 cm petri dish which has a moist filter paper in the bottom and 10 third-instar armyworm larvae about 1 cm long. The dish is covered and held at 26.7° C. After 2 days mortality counts and estimates of the amount of feeding are made. Compounds showing partial kill and/or inhibition of feeding are held for an extra day for further observations.

All compounds showing activity as defined above are retested, using the second leaf on the bean plant, after an interval of 7 days from original treatment, as an assay of residual activity.

Mexican Bean Beetle (*Epilachna varivestis* Mulsant)

Sieva lima bean plants (2 per pot) with primary leaves 7.6 to 10 cm long, are dipped in a 300 ppm solution and set in a hood to dry. One leaf is removed from the plant and placed in a 10 cm petri dish containing a moist filter paper on the bottom and 10 last-instar larvae (13 days from hatching).

The day after treatment, another leaf is removed from the plant and fed to the larvae after removing the remains of the original leaf. Two days after treatment, the third leaf is fed to the larvae, this usually being the last needed. The fourth leaf is used on the third day after treatment if the larvae have not finished feeding. The test is now set aside and held until adults have emerged, usually about 9 days after treatment began. After emergence is complete, each dish is examined for dead larvae, pupae or adults; deformed pupae or adults; larval-pupal intermediates or pupal-adult intermediates; or any other interference with normal molting, transformation and emergence of pupae or adults.

Western Potato Leaf Hopper (*Empoasca abrupta* Delong)

A lima bean plant with the primary leaf expanded to 7.6 to 10 cm is dipped into a 100 ppm solution and set in a hood to dry. A 2.5 cm piece of the tip of 1 leaf is cut off and placed in a 10 cm petri dish with a moist filter paper in the bottom. (In practice, this is usually cut off the tip of a plant from the Mexican bean beetle tests using a bean leaf dipped in the needed solution). From 3 to 10 second-instar nymphs are tapped from the culture plants into the test dish and rapidly covered. Mortality counts are made after two days at 26.7° C.

Malaria Mosquito (*Anopheles quadrimaculatus* Say) Adult Test

Ten ppm solutions are poured into wide-mouth 46.2 ml jars each containing a microscope slide. The slides are removed from the test solution with forceps and laid horizontally to dry on a wide-mouth 118.4 ml bottle. When dry, they are placed in the same 118.4 ml bottle and ten 4 to 5-day old mosquitoes of mixed sexes are added to each bottle. A piece of cotton gauze held on by an elastic band serves as a lid and a wad of cotton soaked in 10% honey solution serves as food. Mortality counts are made after 1 day at 26.7° C.

Bean Aphid (*Aphid fabae* Scopoli)

Five cm fiber pots, each containing a nasturtium plant 5 cm high and infested with 100 to 500 aphids 2 days earlier are placed on a 4 rpm turntable and sprayed with a 100 ppm solution for 2 revolutions with a No. 154 DeVilbiss Atomizer at 1.4 kg/cm$^2$ air pressure. The spray tip is held about 15 cm from the plants and the spray directed so as to give complete coverage of the aphids and the plants. The sprayed plants are laid on their sides on white enamel trays. Mortality estimates are made after 1 day at 26.7° C.

Tobacco Budworm [*Heliothis virescens* (Fabricius)]. Third instar

Three cotton plants with just expanded cotyledons are dipped in a 1000 ppm solution, and placed in a hood to dry. When dry, each cotyledon is cut in half and 10 are each placed in a 29.6 ml plastic medicine cup containing a 1.25 cm dental wick saturated with water, and one third-instar budworm larva is added. The cup is capped and held for 3 days at 26.7° C., after which mortality counts are made.

Cabbage Looper. [*Trichoplusia ni* (Hubner)]

A primary leaf of a cotton plant is dipped in the test solution and agitated for 3 seconds. It is then set in a hood to dry. Following this, the leaf is placed in a 10 cm petri dish containing a moist filter paper at the bottom and 10 third-instar loopers. The dish is covered and held at 26.7° C. After 2 days, mortality counts and estimates of feeding damage are recorded. Those materials showing partial kill and/or inhibition of feeding are held for another day for further observations.

The rating system employed in these tests is as follows:

Rating System

0 = 0–40% killed or affected
1 = reduced feeding (trace to light damage)
2 = some deformed insects (40–80%)
3 = mostly deformed insects (85–100%)
4 = not an index number at present
5 = 41–60% mortality
6 = 61–70% mortality
7 = 71–85% mortality
8 = 86–95% mortality
9 = 100% mortality The absence of a number indicates that no test has been run at that particular dosage.

Compounds rated active (8 or 9) are further tested at reduced concentrations in 50% acetone:50% water.

Data obtained are reported in Table X below.

TABLE Xa
Insecticide evaluation
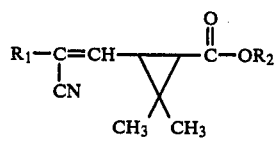
| R₁ | R₂ | Mosquito Larvae ppm | | | Tobacco Budworm Eggs (ppm) | | | Tobacco Budworm Larvae (ppm) | | |
|---|---|---|---|---|---|---|---|---|---|---|
| | | 1.2 | 0.4 | 0.04 | 300 | 100 | 10 | 300 | 100 | 10 |
| phenyl | CMPB | 9 | 9 | 9 | 8 | 0 | | 9 | 9 | 0 |
| phenyl | MPB | 9 | 9 | 0 | 8 | 0 | | 9 | 8 | 0 |
| 4-Cl-phenyl | MPB | 8 | 6 | 0 | 0 | | | 9 | 9 | 0 |
| 4-Cl-phenyl | CMPB | 9 | 9 | 0 | 0 | | | 9 | 9 | 5 |
| thienyl (S) | CMPB | 9 | 9 | 9 | 8 | 0 | | 7 | 0 | |
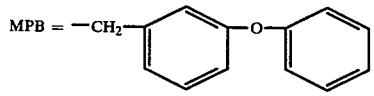
MPB = —CH₂—(3-phenoxyphenyl)
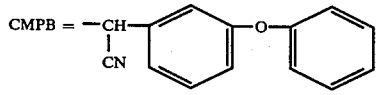
CMPB = —CH(CN)—(3-phenoxyphenyl)
TABLE Xb
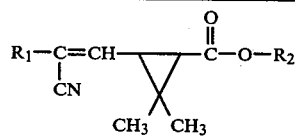
| R₁ | R₂ | 2-Spotted Spider Mites ppm | | Southern Armyworms ppm | | | Mexican Bean Beetle ppm | | |
|---|---|---|---|---|---|---|---|---|---|
| | | 300 | 100 | 1000 | 100 | 10 | 300 | 100 | 10 |
| phenyl | CMPB | 9 | 0 | 9 | 9 | 0 | | | |
| phenyl | MPB | 9 | 0 | 9 | 0 | | | | |

TABLE Xb-continued $$R_1-\underset{CN}{C}=CH-\underset{\underset{CH_3\ CH_3}{\triangle}}{CH}-\underset{O}{\overset{O}{\|}}-O-R_2$$

| R₁ | R₂ | 2-Spotted Spider Mites ppm | | Southern Armyworms ppm | | | Mexican Bean Beetle ppm | | |
|---|---|---|---|---|---|---|---|---|---|
| | | 300 | 100 | 1000 | 100 | 10 | 300 | 100 | 10 |
| 4-Cl-C₆H₄- | CMPB | 9 | 0 | 1 | 0 | | 9 | 8 | 0 |
| 4-CH₃O-C₆H₄- | CMPB | 0 | | 0 | | | 9 | | |
| 2-thienyl | CMPB | 0 | | 9 | 5 | 0 | 9 | 9 | 0 |

MPB = —CH₂—(3-phenoxyphenyl)

CMPB = —CH(CN)—(3-phenoxyphenyl)

TABLE Xc $$R_1-\underset{CN}{C}=CH-\underset{\underset{CH_3\ CH_3}{\triangle}}{CH}-\underset{O}{\overset{O}{\|}}-O-R_2$$

| R₁ | R₂ | Leaf hopper (ppm) | | Mosquito Adult (ppm) | | Bean Aphids (ppm) | | | Tobacco Budworm 3rd Instar (ppm) | | Cabbage Looper (ppm) | |
|---|---|---|---|---|---|---|---|---|---|---|---|---|
| | | 100 | 10 | 10 | 1 | 100 | 10 | 1 | 1000 | 100 | 1000 | 100 |
| C₆H₅- | CMPB | 9 | 7 | 7 | 0 | 9 | 6 | 0 | 6 | 7 | 9 | 5 |
| C₆H₅- | MPB | 9 | 7 | 7 | 0 | 9 | 7 | 0 | 8 | 0 | 0 | 0 |
| 4-Cl-C₆H₄- | MPB | 9 | 0 | 5 | 0 | 9 | 8 | 0 | 5 | 0 | 9 | 1 |
| 4-Cl-C₆H₄- | CMPB | 9 | 5 | 5 | 0 | 9 | 9 | 9 | 8 | 1 | 9 | 9 |
| 4-CH₃O-C₆H₄- | MPB | 5 | 0 | 0 | | 9 | 5 | | 5 | 0 | 5 | 0 |

TABLE Xc-continued $$R_1-\underset{CN}{C}=CH-\underset{\underset{CH_3\ CH_3}{\triangle}}{}\overset{O}{\underset{\|}{C}}-O-R_2$$

| R₁ | R₂ | Leaf hopper (ppm) 100 | 10 | Mosquito Adult (ppm) 10 | 1 | Bean Aphids (ppm) 100 | 10 | 1 | Tobacco Budworm 3rd Instar (ppm) 1000 | 100 | Cabbage Looper (ppm) 1000 | 100 |
|---|---|---|---|---|---|---|---|---|---|---|---|---|
| CH₃O—C₆H₄— | CMPB | 7 | 0 | 0 | | 9 | 6 | 0 | | | | 0 |
| 2,4-Cl₂C₆H₃— | CMPB | 9 | 7 | 0 | | 9 | 8 | 0 | 0 | | — | |
| 2-naphthyl | CMPB | 7 | | 0 | | 8 | 0 | | 1 | | 0 | |
| 2-thienyl | CMPB | 7 | | 0 | | 7 | | | 0 | | 9 | 9 |

MPB = —CH₂—C₆H₄—O—C₆H₅

CMPB = —CH(CN)—C₆H₄—O—C₆H₅

I claim:

1. A compound of the formula:

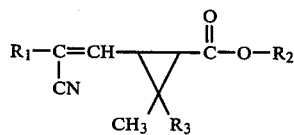

wherein
R₁ is

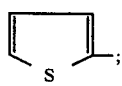

R₂ is 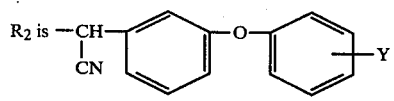

R₃ is hydrogen or methyl; and Y is hydrogen, halogen, methyl or methoxy.

2. A compound according to claim 1, wherein R₃ is methyl.

3. The compound according to claim 1, (E)-trans-3-[2-cyano-2-(2-thienyl)vinyl]-2,2-dimethyl-cyclopropanecarboxylic acid, α-cyano-m-phenoxybenzyl ester.

4. A method for the control of insect pests of agriculturally important crops and ectoparasites of domesticated warm-blooded animals comprising contacting the insects and ectoparasites, or applying to their hosts and to their habitat an insecticidally effective amount compound of the formula:

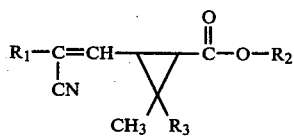

wherein
R₁ is

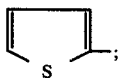

R₂ is 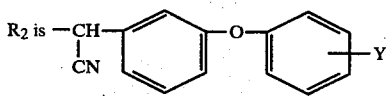

R₃ is hydrogen or methyl; and Y is hydrogen, halogen, methyl or methoxy.

* * * * *